United States Patent
Dutta et al.

(10) Patent No.: US 11,254,637 B2
(45) Date of Patent: Feb. 22, 2022

(54) CONVERSION OF LIGNIN TO IONIC LIQUIDS

(71) Applicant: NATIONAL TECHNOLOGY & ENGINEERING SOLUTIONS OF SANDIA, LLC, Albuquerque, NM (US)

(72) Inventors: Tanmoy Dutta, Berkeley, CA (US); Jian Sun, Albany, CA (US); Blake A. Simmons, San Francisco, CA (US); Seema Singh, Clarksburg, MD (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 0 days.

(21) Appl. No.: 16/308,432
(22) PCT Filed: Jun. 7, 2017
(86) PCT No.: PCT/US2017/036442
§ 371 (c)(1),
(2) Date: Dec. 7, 2018
(87) PCT Pub. No.: WO2017/214334
PCT Pub. Date: Dec. 14, 2017

(65) Prior Publication Data
US 2019/0263748 A1 Aug. 29, 2019

Related U.S. Application Data
(60) Provisional application No. 62/346,919, filed on Jun. 7, 2016.

(51) Int. Cl.
C07C 217/58 (2006.01)
C08H 8/00 (2010.01)
(52) U.S. Cl.
CPC .......... *C07C 217/58* (2013.01); *C08H 8/00* (2013.01); *C07C 2601/16* (2017.05); *H01M 2300/00* (2013.01); *H01M 2300/0045* (2013.01)

(58) Field of Classification Search
None
See application file for complete search history.

(56) References Cited

U.S. PATENT DOCUMENTS

| | | |
|---|---|---|
| 2004/0077519 A1 | 4/2004 | Price et al. |
| 2008/0185112 A1 | 8/2008 | Argyropoulos |
| (Continued) | | |

FOREIGN PATENT DOCUMENTS

| | | |
|---|---|---|
| DE | 102006011077 A1 | 9/2007 |
| WO | 2014/172042 A1 | 10/2014 |

OTHER PUBLICATIONS

Adbel-Magid et al., "Reductive Amination of Aldehydes and Ketones with Sodium Triacetoxyborohydride. Studies on Direct and Indirect Reductive Amination Procedures1", *J. Org. Chem.* 61 (11):3849-3862 (1996).

(Continued)

*Primary Examiner* — Sudhakar Katakam
*Assistant Examiner* — Jennifer C Sawyer
(74) *Attorney, Agent, or Firm* — Kilpatrick Townsend & Stockton LLP

(57) ABSTRACT

Disclosed herein are lignin-derived ionic liquids and methods for preparing them. The methods include forming a reaction mixture comprising a lignin-derived starting material, a carbonyl compound, and an amine; maintaining the reaction mixture under conditions sufficient to form a lignin-derived aminophenol; and converting the lignin derived aminophenol to the lignin-derived ionic liquid. Monomeric phenols, oligomeric phenols, and polymeric phenols can be used as lignin-derived starting materials.

15 Claims, 1 Drawing Sheet

(56) References Cited

U.S. PATENT DOCUMENTS

2012/0011886 A1   1/2012   Shiflett
2015/0135989 A1   5/2015   Raghu
2016/0031843 A1   2/2016   Socha et al.

OTHER PUBLICATIONS

Alhede, et al., "Preparation of 5-[[(2-aminoethyl)thio]methyl]-2-furanmethanol derivative," CAS 110:94977, 1989.
Dizhbite, et al., "Products of lignin modification: promising adsorbents of toxic substances," CAS 139: 86842, 2003.
Foo, et al., "Absorption cycle utilizing ionic compounds and/or non-ionic absorbents as working fluids," CAS 167:382562, 2016.
Liang, et al., "Synthesis and characterization of quaternary ammonium-based ionic liquids," CAS 157: 437855, 2012.
Pratap, et al., "Preparation of (R)-(−)- / (S)-(+) -7- [3-n-substituted amino-2-hydroxypropoxy] flavones as antidyslipidemic agents," CAS 148: 238941, 2008.
PubChem CID 124128814, Create Date: Feb. 18, 2017, 11 pages.
Shiflett, et al., "Ionic compounds in lithium bromide/water absorption cycle systems," CAS 167: 382565, 2016.
Socha, et al., "Efficient biomass pretreatment using ionic liquids derived from lignin and hemicellulose," PNAS, published online Aug. 18, 2014, E3587-E3595.
Srinivasan, et al., "Process for preparation of ezetimibe," CAS 152: 97325, 2009.
Holladay et al. *Top Value-Added Chemicals from Biomass—vol. II—Results of Screening for Potential Candidates from Biorefinery Lignin*, PNNL-16983; Pacific Northwest National Laboratory Richland, WA, 2007.

CONVERSION OF LIGNIN TO IONIC LIQUIDS

CROSS-REFERENCES TO RELATED APPLICATIONS

The present application is a U.S. National Phase of International Application No. PCT/US2017/036442, filed Jun. 7, 2017, which claims priority to U.S. Provisional Pat. Appl. No. 62/346,919, filed Jun. 7, 2016, which is incorporated herein by reference in its entirety.

STATEMENT AS TO RIGHTS TO INVENTIONS MADE UNDER FEDERALLY SPONSORED RESEARCH AND DEVELOPMENT

This invention was made with government support under Contract No. DE-AC02-05CH11231 awarded by the United States Department of Energy. The government has certain rights in the invention.

BACKGROUND OF THE INVENTION

Lignin and hemicellulose roughly constitute ~50% mass of any plant biomass. Lignin is one of the most abundant biopolymers. The lignin and hemicellulose are the main byproducts of the paper and pulp industry and the biorefinery. Unfortunately there is no proper application of lignin byproducts apart from generation of heat. Ionic liquids (ILs) are used as powerful solvents (in chemical reactions, biomass pretreatment, and the like), electrolytes, heat transfer liquids, and various other important applications. Development of a simple and economic route to synthesize ionic liquids from the lignin, hemicellulose, and their depolymerized products will not only reduce ionic liquid production cost but also will demonstrate a route to synthesize ionic liquids from renewable resources.

What is desired is a process which can convert lignin and their depolymerized products (both monomeric and oligomeric) in simple, inexpensive and in fewer synthetic steps to ILs. It is also desirable to change the structure of the cation and the anions to tailor made the ILs suitable for various applications, such as solvents for chemical reactions, biomass pretreatment, batteries, electrolytes, and the like. Methods for the synthesis of tertiary amine-based ILs from aromatic aldehydes, derived from lignin and hemicellulose, have recently been developed. The current route to transform aldehyde to tertiary amine-based ILs is achieved via two-step process including imine formation and reductive amination, which requires reagents such as sodium triacetoxyborohydride reagent (~$127/100 g). New methods for ionic liquid preparation with fewer steps and lower overall cost are needed. The present invention addresses this need.

BRIEF SUMMARY OF THE INVENTION

Exemplary embodiments provided in accordance with the presently disclosed subject matter include, but are not limited to, the claims and the following embodiments:

1. A method for preparing a lignin-derived ionic liquid, the method comprising:
   forming a reaction mixture comprising a lignin-derived starting material, a carbonyl compound, and an amine;
   maintaining the reaction mixture under conditions sufficient to form a lignin-derived aminophenol; and
   converting the lignin derived aminophenol to the lignin-derived ionic liquid.

2. The method of embodiment 1, wherein the lignin-derived starting material is comprises an monomeric phenol, an oligomeric phenol, a polymeric phenol, or combinations thereof.

3. The method of embodiment 1 or embodiment 2, wherein the carbonyl compound is a ketone or an aldehyde.

4. The method of embodiment 3, wherein the carbonyl compound is an aldehyde.

5. The method of any one of embodiments 1-4, wherein the amine is a primary amine or a secondary amine.

6. The method of embodiment 5, wherein the amine is a secondary amine.

7. The method of embodiment 6, wherein the secondary amine is diethylamine.

8. The method of any one of embodiments 1-7, wherein the reaction mixture further comprises a solvent.

9. The method of embodiment 8, wherein the solvent is water.

10. The method of any one of embodiments 1-7, wherein the reaction mixture consists of the lignin-derived starting material, the carbonyl compound, and the amine.

11. The method of any one of embodiments 1-10, wherein the reaction mixture is maintained at a temperature ranging from about 25° C. to about 250° C. for a period of time ranging from about 5 minutes to about 24 hours.

12. The method of embodiment 10, wherein the reaction mixture is maintained at a temperature ranging from about 40° C. to about 80° C. for a period of time ranging from about 2 hours to about 8 hours.

13. The method of any one of embodiments 1-12, wherein converting the lignin-derived aminophenol to the ionic liquid comprises contacting the lignin-derived aminophenol with an acid.

14. The method of embodiment 13, wherein the acid is hydrochloric acid, sulfuric acid, or a combination thereof.

15. The method of any one of embodiments 1-14, further comprising isolating at least a portion of the ionic liquid.

16. The method of embodiment 15, wherein isolating the ionic liquid comprising precipitating the ionic liquid.

17. An ionic liquid prepared according to the method of any one of embodiments 1-16.

18. An ionic liquid comprising at least one compound according to Formula I:

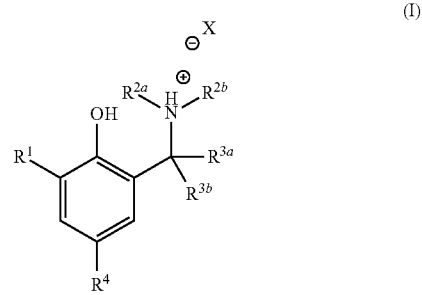

wherein:
$R^1$ is selected from the group consisting of —$OR^{1a}$ and hydrogen;
$R^{1a}$ is selected from the group consisting of $C_{1-6}$ alkyl and hydrogen;
$R^{2a}$ is selected from the group consisting of $C_{1-12}$ alkyl, $C_{2-12}$ alkenyl, $C_{2-12}$ alkynyl, $C_{3-12}$ cycloalkyl, and $C_{6-14}$ aryl;

$R^{2b}$ is selected from the group consisting of $C_{1-12}$ alkyl, $C_{2-12}$ alkenyl, $C_{2-12}$ alkynyl, $C_{3-12}$ cycloalkyl, $C_{6-14}$ aryl, and hydrogen;

$R^{3a}$ and $R^{3b}$ are independently selected from the group consisting of hydrogen, $C_{1-12}$ alkyl, $C_{2-12}$ alkenyl, $C_{2-12}$ alkynyl, $C_{3-12}$ cycloalkyl, and $C_{6-14}$ aryl;

$R^4$ is selected from the group consisting of a polymeric lignin residue, an oligomeric lignin residue, a guaiacol residue, a syringol residue, a hydroxyphenol residue, $C_{1-12}$ alkyl, $C_{1-12}$ alkoxy, $C_{2-12}$ alkenyl, $C_{2-12}$ alkynyl, and hydrogen; and X is an anion.

19. The ionic liquid of embodiment 18, wherein $R^1$ is selected from the group consisting of —$OCH_3$ and hydrogen.

20. The ionic liquid of embodiment 18 or embodiment 19, wherein $R^{2a}$ and $R^{2b}$ are independently selected $C_{1-6}$ alkyl.

21. The ionic liquid of any one of embodiments 18-20, wherein $R^{3a}$ and $R^{3b}$ are hydrogen.

22. The ionic liquid of any one of embodiments 18-21, wherein $R^4$ is selected from the group consisting of an oligomeric lignin residue and a polymeric lignin residue.

23. The ionic liquid of any one of embodiments 18-21, wherein $R^4$ is selected from the group consisting of a guaiacol residue, a syringol residue, and a hydroxyphenol residue.

24. The ionic liquid of any one of embodiments 18-23, wherein X is selected from the group consisting of fluoride, chloride, bromide, a phosphate, a sulfate, a carboxylate, a fluorophosphate, and a fluoroborate.

25. The ionic liquid of embodiment 24, wherein X is selected from the group consisting of chloride (Cl$^-$) and hydrogen sulfate (HSO$_4^-$).

26. The ionic liquid of any one of embodiments 18-25, comprising two or more different compounds according to Formula I.

DETAILED DESCRIPTION OF THE INVENTION

Figure 1:
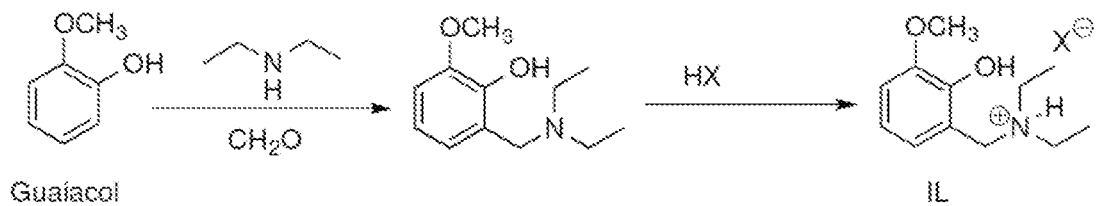
FIG. 1 shows the synthesis of guaiacol-based ionic liquids.
Figure 2:
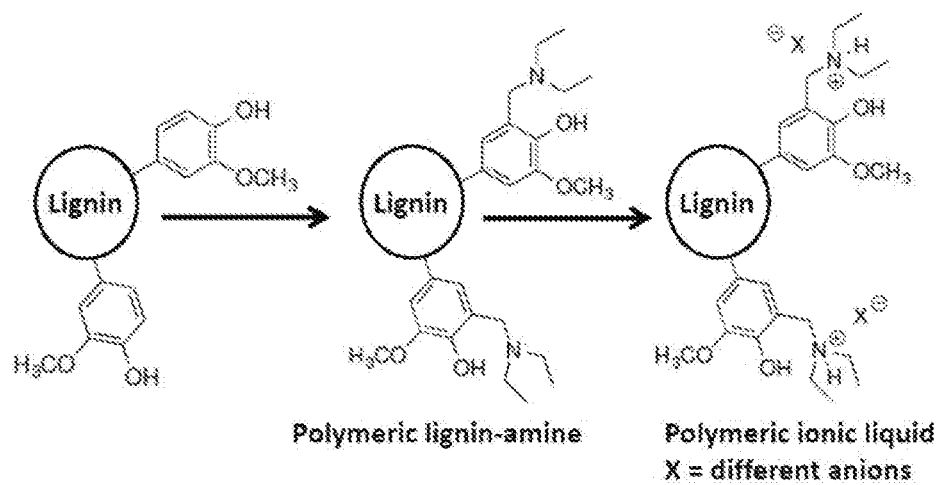
FIG. 2 shows the synthesis of lignin-based polymeric ionic liquids (X=Cl, HSO$_4$).
Figure 3:
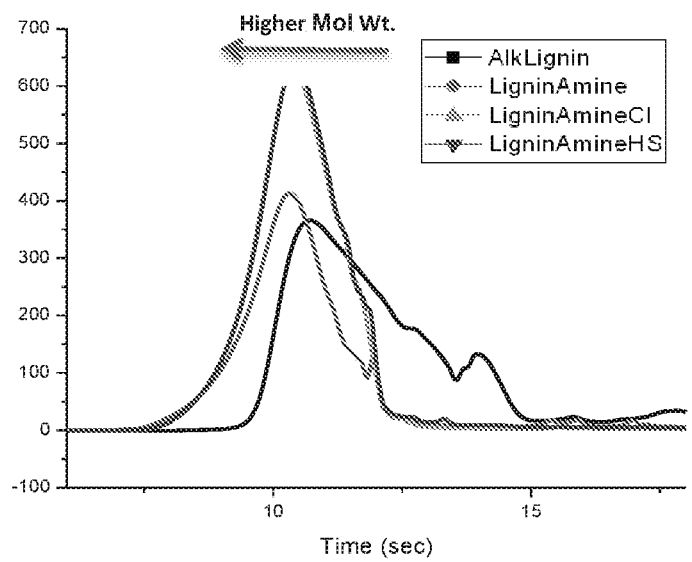
FIG. 3 shows an SEC elugram showing increase in the lignin molecular weight for lignin amine and lignin-based polymeric ILs (Lignin Amine Cl and Lignin amine HS) as compared to starting lignin.

The present invention provides for a composition comprising a polymeric ionic liquid (IL) derived from lignin depolymerized products, such as phenolic monomers, phenolic oligomers, and phenolic polymers. In some embodiments, the lignin depolymerized products are derived from biomass.

The present invention provides for a method for easily convert lignin depolymerized phenolic monomers and/or polymeric/oligomeric lignin into IL. The method is a direct route to synthesize ILs from lignin and depolymerized lignin products.

Advantages of the present invention include one or more of the following:

The method is capable of transforming monomeric phenolic lignin depolymerized products or oligomeric and polymeric lignin to ionic liquids (e.g., tertiary amine salts) via a Mannich-type reaction. Phenols are the one of the most abundant functional groups in lignin and its depolymerized products.

The method only requires cheap solvent, chemicals, and relatively simple reaction conditions. The IL synthesis is a convenient two-step synthesis which requires minimal purification or no purification. The two synthetic steps can easily conducted as a one pot process, which can be readily applied to a complex mixture of depolymerized products, oligomeric lignin, or even polymeric lignin.

The invention also provides a simple, cost effective route to synthesize ILs from guaiacol, which is the most abundant depolymerized product irrespective of the depolymerization method.

The present invention represents a route to synthesize IL from lignin that does not require chemical oxidation steps and is widely applicable to lignin and their depolymerized products.

I. DEFINITIONS

As used herein, the term "lignin" refers to a phenylpropane polymer of monolignol monomers (p-coumaryl alcohol, coniferyl alcohol, and sinapyl alcohol) found as an integral part of the secondary cell walls of plants and certain types of algae. The term "lignin-derived," as it is used to herein to refer to a starting material, ionic liquid, or other material, means that the material can be obtained by converting lignin to the material. Conversion of lignin to a lignin-derived material can be accomplished by chemical, biochemical, and/or physical means as described herein. The term "lignin-derived starting material" includes lignin itself (e.g., a technical lignin). The term "lignin residue" refers to a radical derived from a lignin or lignin depolymerization product; the lignin residue is covalently bonded to a functional group (e.g., an aminophenol group) in the ionic liquids and other compounds disclosed herein. A lignin residue can be bonded via a carbon atom or oxygen atom of the residue.

As used herein the term "phenol" refers to a compound containing at least one hydroxybenzene radical, i.e., a hydroxyphenyl group. Lignins of all sorts are therefore considered to be phenols for the purposes of this disclosure. Phenols include, but are not limited to, compounds containing with one or more 2-hydroxyphenyl groups, 3-hydroxyphenyl groups, and/or 4-hydroxyphenyl groups (also referred to as p-hydroxyphenyl groups). Phenols can contain unsubstituted hydroxy phenyl groups, e.g., unsubstituted p-hydroxyphenyl groups, or substituted hydroxyphenyl groups. Examples of substituted hydroxyphenyl groups include, but are not limited to, guaiacyl (i.e., 3-methoxy-4-hydroxyphenyl) groups and syringyl (i.e., 3,5-dimethoxy-4-hydroxyphenyl) groups.

Lignin-derived phenols typically contain further aromatic functional groups derived from the three principal biosynthetic precursors of lignin p-coumaryl alcohol, coniferyl alcohol, and sinapyl alcohol. These further aromatic functional groups include, but are not limited to, crosslinked guaiacyl groups, crosslinked syringyl groups, and/or crosslinked p-hydroxyphenyl groups, joined together by one or more di- and tri-radical linking groups such as 1,3-dihydroxy-propandiyl moieties, tetrahydro-1H,3H-furo[3,4-c]furandiyl moieties, 3-(hydroxymethyl)-2,3-dihydrobenzofurandiyl moieties, 6-(hydroxymethyl)-6,7-dihydrodibenzo[e,g][1,4]dioxocintriyl moieties, and the like. Although the actual structure of lignin cannot be generalized as a single formula, representative structures of lignin and lignin-derived phenols are disclosed, for example, by Tolbert et al.

("Characterization and analysis of the molecular weight of lignin for biorefining studies." *Biofuels, Bioprod. Bioref.* 2014, 8(6): 836-856), Lapierre et al. ("New insights into the molecular architecture of hardwood lignins by chemical degradative methods." *Res Chem Intermediate.* 1995, 21: 397-412), and Sakakibara ("A structural model of softwood lignin." *Wood Sci Technol.* 1980, 14:89-100), which are incorporated herein by reference.

As used herein, the term "polymeric phenol" refers to a polymer containing one or more phenol groups, e.g., one or more crosslinked guaiacyl groups, and/or one or more crosslinked syringyl groups, and/or one or more crosslinked p-hydroxyphenyl groups. Polymeric phenols generally range from about 1,000 g mol$^{-1}$ to about 100,000 g mol$^{-1}$ in molecular weight (i.e., weight average molecule weight "$M_w$").

As used herein, the term "oligomeric phenol" refers to a compound containing from about 2 to about 10 phenol groups, e.g., 2-10 crosslinked guaiacyl groups, and/or 2-10 crosslinked syringyl groups, and/or 2-10 crosslinked p-hydroxyphenyl groups. Oligomeric phenols generally range from about 200 g mol$^{-1}$ to about 1,000 g mol$^{-1}$ in molecular weight ($M_w$).

As used herein, the term "monomeric phenol" refers to a compound containing one and only one hydroxyphenyl group. The hydroxyphenyl group can be substituted or unsubstituted as described above.

As used herein, the term "carbonyl compound" refers to a compound having a carbonyl moiety (i.e., a C=O bond) including, but not limited to, compounds of the formula C(O)R$^a$R$^b$, wherein R$^a$ and R$^b$ are independently selected from hydrogen, $C_{1-12}$ alkyl, $C_{1-12}$ alkenyl, $C_{2-12}$ alkynyl, $C_{3-12}$ cycloalkyl, and $C_{6-14}$ aryl. Examples of carbonyl compounds include but are not limited to aldehydes, wherein one or both of R$^a$ and R$^b$ are hydrogen, and ketones, wherein R$^a$ and R$^b$ are both other than hydrogen.

As used herein, the term "amine" refers to a compound having a substituted nitrogen atom including, but not limited to, compounds of the formula NHR$^c$R$^d$ wherein R$^c$ is selected from $C_{1-12}$ alkyl, $C_{2-12}$ alkenyl, $C_{2-12}$ alkynyl, $C_{3-12}$ cycloalkyl, and $C_{6-14}$ aryl, and wherein R$^d$ is selected front $C_{1-12}$ alkyl, $C_{2-12}$ alkenyl, $C_{2-12}$ alkynyl, $C_{3-12}$ cycloalkyl, $C_{6-14}$ aryl, and hydrogen. The amine can be a primary amine, wherein R$^d$ is hydrogen, or a secondary amine, wherein R$^d$ is other than hydrogen.

As used herein, the term "lignin-derived aminophenol" refers to a polymeric phenol, oligomeric phenol, or monomeric phenol as described above, which is substituted with one or more —NR$^c$R$^c$ groups, wherein R$^c$ is selected front $C_{1-12}$ alkyl, $C_{2-12}$ alkenyl, $C_{2-12}$ alkynyl, $C_{3-12}$ cycloalkyl, and $C_{6-14}$ aryl, and wherein R$^d$ is selected from $C_{1-12}$ alkyl, $C_{2-12}$ alkenyl, $C_{2-12}$ alkynyl, $C_{3-12}$ cycloalkyl, $C_{6-14}$ aryl, and hydrogen. The amino group and the hydroxy group can be present on neighboring carbon atoms of the phenyl ring (i.e., in the ortho arrangement with respect to one another), or they can be separated by one carbon atom of the phenyl ring (i.e., in the meta arrangement) or two carbon atoms of the phenyl ring (i.e., in the para arrangement).

As used herein, the term "alkyl," by itself or as part of another substituent, refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, hexyl, etc. Alkyl can also refer to alkyl groups having up to 20 carbons atoms, such as, but not limited to heptyl, octyl, nonyl, decyl, etc.

As used herein, the term "alkoxy," by itself or as part of another substituent, refers to a radical —OR', wherein R' is an alkyl group as defined above.

As used herein, the term "alkenyl," by itself or as part of another substituent, refers to a straight chain or branched hydrocarbon having at least 2 carbon atoms and at least one double bond. Alkenyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Alkenyl groups can have any suitable number of double bonds, including, but not limited to, 1, 2, 3, 4, 5 or more. Examples of alkenyl groups include, but are not limited to, vinyl (ethenyl), propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl.

As used herein, the term "alkynyl," by itself or as part of another substituent refers, to either a straight chain or branched hydrocarbon having at least 2 carbon atoms and at least one triple bond. Alkynyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{3-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Examples of alkynyl groups include, but are not limited to, acetylenyl, propynyl, 1-butynyl, 2-butynyl, isobutynyl, sec-butynyl, butadiynyl, 1-pentynyl, 2-pentynyl, isopentynyl, 1,3-pentadiynyl, 1,4-pentadiynyl, 1-hexynyl, 2-hexynyl, 3-hexynyl, 1,3-hexadiynyl, 1,4-hexadiynyl, 1,5-hexadiynyl, 2,4-hexadiynyl, or 1,3,5-hexatriynyl.

As used herein, the term "cycloalkyl," by itself or as part of another substituent, refers to a saturated or partially unsaturated, monocyclic, fused bicyclic or bridged polycyclic ring assembly containing from 3 to 12 ring atoms, or the number of atoms indicated. Cycloalkyl can include any number of carbons, such as $C_{3-6}$, $C_{4-6}$, $C_{5-6}$, $C_{3-8}$, $C_{4-8}$, $C_{5-8}$, $C_{6-8}$, $C_{3-9}$, $C_{3-10}$, $C_{3-11}$, and $C_{3-12}$. Saturated monocyclic cycloalkyl rings include, for example, cyclopropyl, cyclobutyl, cyclopentyl, cyclohexyl, and cyclooctyl. Saturated bicyclic and polycyclic cycloalkyl rings include, for example, norbornane, [2.2.2] bicyclooctane, decahydronaphthalene and adamantane. Cycloalkyl groups can also be partially unsaturated, having one or more double or triple bonds in the ring. Representative cycloalkyl groups that are partially unsaturated include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbornene, and norbornadiene. When cycloalkyl is a saturated monocyclic $C_{3-8}$ cycloalkyl, exemplary groups include, but are not limited to cyclopropyl, cyclobutyl, cyclopentyl, cyclohexyl, cycloheptyl and cyclooctyl. When cycloalkyl is a saturated monocyclic $C_{3-6}$ cycloalkyl, exemplary groups include, but are not limited to cyclopropyl, cyclobutyl, cyclopentyl, and cyclohexyl.

As used herein, the term "aryl," by itself or as part of another substituent, refers to an aromatic ring system having any suitable number of carbon ring atoms and any suitable number of rings. Aryl groups can include any suitable number of carbon ring atoms, such as $C_6$, $C_7$, $C_8$, $C_9$, $C_{10}$, $C_{11}$, $C_{12}$, $C_{13}$, $C_{14}$, $C_{15}$ or $C_{16}$, as well as $C_{6-10}$, $C_{6-12}$, or $C_{6-14}$. Aryl groups can be monocyclic, fused to form bicyclic (e.g., benzocyclohexyl) or tricyclic groups, or linked by a bond to form a biaryl group. Representative aryl groups include phenyl, naphthyl and biphenyl. Other aryl groups include benzyl, having a methylene linking group. Some aryl groups have from 6 to 12 ring members, such as phenyl, naphthyl or biphenyl. Other aryl groups have from 6 to 10 ring members, such as phenyl or naphthyl. Some other aryl groups have 6 ring members, such as phenyl.

As used herein, the terms "halo" and "halogen," by themselves or as part of another substituent, refer to a fluorine, chlorine, bromine, or iodine atom.

As used herein, the term "ionic liquid" refers to an organic salt that is a liquid at room temperature rather than a solid or crystalline substance. Ionic liquids typically exhibit a number of advantageous properties, including low volatility, thermal stability, and the ability to dissolve a wide range of solutes under mild conditions. The term "lignin-derived ionic liquid" refers to any ionic liquid containing cations (e.g., tertiary amines or quaternary amines) or anions (e.g., deprotonated carboxylic acids) that are prepared from lignin-based starting materials (e.g., a polymeric, oligomeric, or monomeric phenol).

As used herein, the term "acid" refers to a substance that is capable of donating a proton (i.e., a hydrogen cation) to form a conjugate base of the acid. Examples of acids include, but are not limited to, hydrochloric acid, sulfuric acid, acetic acid, and formic acid.

As used herein, the terms "contacting" and "forming a reaction mixture" refer to the process of bringing into contact at least two distinct species such that they can react. It should be appreciated, however, that the resulting reaction product can be produced directly from a reaction between the added reagents or from an intermediate from one or more of the added reagents which can be produced in the reaction mixture.

The terms "about" and "around," as used herein to modify a numerical value, indicate a close range surrounding that explicit value. If "X" were the value, "about X" or "around X" would indicate a value from 0.9X to 1.1X. "About X" thus includes, for example, a value from 0.95X to 1.05X, or from 0.98X to 1.02X, or from 0.99X to 1.01X. Any reference to "about X" or "around X" specifically indicates at least the values X, 0.90X, 0.91X, 0.92X, 0.93X, 0.94X, 0.95X, 0.96X, 0.97X, 0.98X, 0.99X, 1.01X, 1.02X, 1.03X, 1.04X, 1.05X, 1.07X, 1.08X, 1.09X, and 1.10X. Accordingly, "about X" and "around X" are intended to teach and provide written description support for a claim limitation of, e.g., "0.98X."

II. METHODS FOR PREPARING LIGNIN-DERIVED IONIC LIQUIDS

In one aspect, the invention provides a method for preparing a lignin-derived ionic liquid. The method includes:
  forming a reaction mixture comprising a lignin-derived starting material, a carbonyl compound, and an amine;
  maintaining the reaction mixture under conditions sufficient to form a lignin-derived aminophenol; and
  converting the lignin derived aminophenol to the lignin-derived ionic liquid.

Lignin is a phenylpropane polymer of monolignol monomers. It is generally found as an integral part of the secondary cell walls of plants and certain types of algae. There are three monolignol monomers, methoxylated to various degrees: p-coumaryl alcohol, coniferyl alcohol, and sinapyl alcohol. These lignols are incorporated into lignin in the form of the phenylpropanoids p-hydroxyphenyl (H), guaiacyl (G), and syringyl (S), respectively. Gymnosperms have a lignin that consists almost entirely of G with small quantities of H. That of dicotyledonous angiosperms is more often than not a mixture of G and S (with very little H), and monocotyledonous lignin is a mixture of all three. Many grasses have mostly G, while some palms have mainly S. Lignins generally contain small amounts of incomplete or modified monolignols, and other monomers are prominent in non-woody plants. Unlike cellulose and hemicellulose, lignin cannot be depolymerized by hydrolysis. Cleavage of the principal bonds in the lignin polymer generally proceeds through oxidation.

In some embodiments, the lignin is provided as lignocellulosic biomass. As used herein, the phrase "biomass" refers to lignocellulosic materials comprised of lignin-containing any mix of cellulose, hemicelluloses, and lignin as the major constituents. In the context of this invention "lignocellulosic biomass" is used interchangeably with "cellulosic biomass". Both terms refer to biomass that comprises lignin. "Biomass" for use in the process of the present invention includes any biomass or mixtures thereof that contains lignin or lignocellulose. Lignocellulose-containing biomass primarily consists of cellulose, hemicelluloses, and lignin. Woody biomass, for instance, is about 45-50% cellulose, 20-25% hemicellulose and 20-25% lignin. Herbaceous materials have lower cellulose, lower lignin and higher hemicellulose contents.

Cellulose is a linear $\beta$1-4 linked polymer of glucose. It is the principal component of all higher plant cell walls. In nature, cellulose exists in crystalline and amorphous states. The thermodynamic stability of the $\beta$1-4 linkage and the capacity of cellulose to form internal hydrogen bonds gives it great structural strength. Cellulose is degraded to glucose through hydrolytic cleavage of the glycosidic bond. Hemicellulose is a term used to refer to a wide variety of heteropolysaccharides found in association with cellulose and lignin in both woody and herbaceous plant species. The sugar composition varies with the plant species, but in angiosperms, the principal hemicellulosic sugar is xylose. Like cellulose, xylose occurs in the $\beta$1-4 linked backbone of the polymer. In gymnosperms, the principal component sugar is mannose. Arabinose is found as a side branch in some hemicelluloses.

In a some embodiments, the lignocellulosic biomass includes, but is not limited to, switchgrass, pine, eucalyptus, corn stover, corn fiber, hardwood, such as poplar and birch, softwood, cereal straw, such as, wheat straw, switch grass, Miscanthus, rice hulls, or mixtures thereof. Other examples include corn fiber, rice straw, wheat bran, pine wood, wood chips, poplar, bagasse, paper and pulp processing waste.

In some embodiments, the lignin is obtained via chemical or enzymatic hydrolysis of lignocellulosic biomass. For example, lignocellulosic biomass can be treated with hot water, carbon dioxide, acid, or base, or a combination thereof in order to obtain lignin from the biomass. Ionic liquids (including, but not limited to, 1-ethyl-3-methylimidazolium acetate) can be used in treatment methods to dissolve biomass and recover lignin and cellulose for further processing as described, for example, in U.S. Pat. Appl. Pub. No. 2012/0301948 and Intl. Pat. Appl. Pub. No. WO 2016/070125, which are incorporated herein by reference. Biomass can also be subjected to the action of one or more proteases, lipases, cellulases, amylases, glucano-hydrolases, pectinases, xylanases, ferulic acid esterases, mannanases, or hemicellulases. The pretreated biomass may also be treated with other enzymes, e.g., hemicellulases, that are used for the degradation of biomass.

A "cellulase" as used herein is a glycoside hydrolase enzyme that hydrolyzes cellulose ($\beta$-1,4-glucan or $\beta$-D-glucosidic linkages) resulting in the formation of glucose, cellobiose, cellooligosaccharides, and the like, in the context of the present invention, cellulases include endoglucanases; exoglucanases or cellobiohydrolases; and β-glucosidases. Endoglucanases (EC 3.2.1.4) including endo-1,4-β-glucanases or 1,4-β-D-glucan-4-glucanohydrolases, act randomly on soluble and insoluble 1,4-β-glucan substrates. Exoglucanases (exo-1,4-β-D-glucanases, e.g., the 1,4-β-D-glucan glucohydrolases; EC 3.2.1.74) liberate D-glucose from 1,4-β-D-glucans and hydrolyze D-cellobiose slowly. Cellobiohydrolases (1,4-β-D-glucan cellobiohydrolases, EC 3.2.1.91) liberate D-cellobiose from 1,4-β-glucans. β-Glucosidases ([β]-D-glucoside glucohydrolase; β-D-glucosidases; EC 3.2.1.21) act to release D-glucose units from cellobiose and soluble cellodextrins, as well as an array of glycosides. Endoglucanases act mainly on the amorphous parts of the cellulose fiber, whereas cellobiohydrolases are also able to degrade crystalline cellulose.

A combination of two or more cellulases can be used to catalyze the hydrolysis of cellulose-containing substrates. For example, endoglucanases break internal bonds and disrupt the crystalline structure of cellulose, exposing individual cellulose polysaccharide chains ("glucans"). Cellobiohydrolases incrementally shorten the glucan molecules, releasing mainly cellobiose units (a water-soluble β-1,4-linked dimer of glucose) as well as glucose, cellotriose, and cellotetrose. β-glucosidases split the cellobiose into glucose monomers. The cellulase can be a thermostable cellulose.

Cellulases suitable for use in the present invention are commercially available from, for example, Genencor (USA) and Novozymes (Europe). For instance, Novozyme has a number of different enzymes and enzyme complexes that are specifically designed to be useful for the hydrolysis of lignocellulosic materials. Examples include, but are not limited to, the following: NS50013, which is a cellulase; NS50010, which is a β-glucosidase; NS22086, which is a cellulase complex; NS22086, which is a xylanase; NS22118, which is β-glucosidase; NS22119, which is an enzyme complex of carbohydrases, including arabinase, β-glucanase, cellulase, hemicellulase, pectinase, and xylanase; NS22002, which is a mixture of β-glucanase and xylanase, and NS22035, which is a glucoamylase. In addition, suitable thermostable cellulases are disclosed in U.S. Pat. No. 9,322, 042 and PCT International Publication No. WO 2010/ 124266, which is incorporated herein by reference. Other hydrolases suitable for hydrolyzing the pretreated biomass, i.e., the lignocellulosic material, will be known to those of skill in the art. See, e.g., Viikari et al. *Adv. Biochem. Eng. Biotechnol.,* 108:121-45, 2007; and U.S. Pat. Nos. 8,017, 361; 8,017,373; and 8,318,461; which are incorporated herein by reference.

In some embodiments, biomass is mechanically ground, chipped, cracked, fractured, steam-exploded, ammonia fiber expanded, and/or crushed to provide lignin for use in the methods of the invention. In some such embodiment, these techniques are combined with enzymatic hydrolysis to provide the lignin-derived starting materials.

In some embodiments, the lignin-derived starting material is a technical lignin. Technical lignins are most commonly derived as a byproduct of the paper and pulp industry. For example, kraft lignin may be obtained via the kraft process; lignosulfonates, may be produced, e.g., from the sulfite pulping process; alkali lignin, may be produced, e.g., from treating the black liquor from the soda process with acid; and low sulfonate alkali lignin may be obtained as a byproduct of wood pulping. It is understood by those in the art that the precise source for technical lignin is not critical for the methods of the invention. Rather, starting materials from a wide range of polymeric lignin sources can be employed. In some embodiments, the technical lignin is selected from the group consisting of kraft lignin, lignosulfate, alkali lignin, and combinations thereof. In some embodiments, the technical lignin is bagasse lignin, poplar lignin, or a combination thereof. In some embodiments of the invention, the lignin (e.g., a technical lignin) is mechanically ground, chipped, cracked, fractured, or crushed.

In some embodiments, the lignin-derived starting material is a polymeric phenol. The terms "lignin" and "polymeric phenol" are used interchangeably to refer to polymeric compounds containing one or more crosslinked guaiacyl groups, and/or one or more crosslinked syringyl groups, and/or one or more crosslinked p-hydroxyphenyl groups. In general, polymeric phenols will range in molecular weight (i.e., weight average molecule weight "$M_w$") from about 1,000 g mol$^{-1}$ to 100,000 g mol$^{-1}$, depending on the source of the lignin-derived starting material and the method used for isolated the starting material from a biomass source.

Lignin can also be depolymerized to provide oligomeric phenols and monomeric phenols for use as lignin-derived starting materials in the methods of the invention. Processes and agents suitable for depolymerizing lignin include those described in, e.g., by Pandey (*Chem. Eng. Technol.* 2001, 34(1): 29-41); Pearl (*J. Am. Chem. Soc.* 1942, 64 (6):1429-1431); Liu (*RSC Adv.* 2013, 3: 5789-5793); Kleen (*J. Anal. Appl. Pyrolysis.* 1991, 19: 139); and Xiang (*Appl. Biochem. Biotechnol.,* 2000, 153: 84-86), and International Pat. Appl. Publ. No. WO 2014/17204, which are incorporated herein by reference. Oxidative depolymerization methods can provide phenolic starting materials containing aldehydes, alcohols, and acids; steam explosion which provides the hemicellulose depolymerization and dehydration product furfural or 5-hydroxymethylfurfural; contacting with ionic liquids and a catalyst which provides phenols; and oxidative methods or pyrolysis with hydrogen which provide aldehydes, alcohols, and carboxylic acids.

Examples of lignin depolymerization agents for obtaining lignin-derived starting materials include, but are not limited to, ionic liquids or ionic liquid mixtures (including the ionic liquids or ionic liquid mixtures of the invention), hydrogenolysis (e.g., $H_2$ gas, a hydrogen donating agent such as tetralin, sodium formate, or formic acid), a dilute acid, a concentrated acid, a base, an oxidizing agent (e.g., nitrobenzene, a metal oxide, hydrogen peroxide, or $O_2$ gas with an appropriate catalyst), Fenton's reagent ($H_2O_2$ and ferrous sulfate), metal organic frameworks of copper or iron, and ammonium hydroxide.

As a nonlimiting example, lignin or lignocellulosic biomass may be contacted with $CuSO_4$ and NaOH under conditions that yield aldehydes. Lignin or lignocellulosic biomass may also be contacted with quaternary ammonium and imidazolium dimethylphosphate ionic liquids. In addition, lignin or lignocellulosic biomass may be contacted with mild oxidants such as nitrobenzene, metal oxides, and oxygen to produce aldehydes. Similarly, depolymerization with metal organic frameworks of $Cu^{2+}$, $Fe^{3+}$, or combinations of metal ions can be used as oxidants for lignin depolymerization. Alternatively, hydrogen peroxide or Fenton's reagent may be utilized for oxidative lignin depolymerization. As yet another embodiment, oxidation may be performed under alkaline conditions.

Pyrolysis can also be employed for lignin depolymerization. In some cases, fast pyrolysis depolymerization can provide alcohols such as 4-methyl guaiacol, 4-vinyl guaiacol, trans-isoeugenol, trans-coniferyl alcohol, and aldehydes such as vanillin, and coniferaldehyde as the predominant products of lignin depolymerization. In some instances, fast pyrolysis can result in alcohols such as guaiacol, 4-vinyl guaiacol, and trans-isoeugenol as the predominant products of lignin depolymerization. In some instances, pyrolysis can provide guaiacol, syringol, and 4-vinyl syringol as the predominant products of lignin depolymerization.

In some instances, hydrogenolysis can provide phenols for use as starting materials in the methods of the invention. Hydrogenolysis can be performed, for example, at about 300-600° C. in the presence of hydrogen gas or a hydrogen donor. Suitable hydrogen donors include, but are not limited to, tetralin, sodium formate, formic acid, and the like.

Base catalyzed depolymerization can also be employed, such as described in U.S. Pat. No. 5,959,167. For example, the lignin can be contacted with a base (e.g., an alkali hydroxide) in the presence of a supercritical alcohol (e.g., methanol, ethanol, etc.). In some cases, the base catalyzed depolymerization can provide a mixture of depolymerized lignin products including alkylated phenols (e.g., mono, di, tri, and polysubstituted phenols and alkylated benzenes), alkylated benzenes, and alkoxybenzenes.

In some embodiments, the depolymerization products can be directly converted by subsequent methods of the present invention into ions suitable for ionic liquid formation without extensive purification. For example, lignin may be depolymerized and converted to an aminophenol or ionic liquid without purifying, or substantially purifying, the depolymerization products from other components of lignocellulosic biomass. Alternatively, lignin may be depolymerized and the depolymerization products can be purified. Methods and compositions are known in the art for purifying lignin depolymerization products.

In some embodiments, the invention provides methods as described above wherein the lignin-derived starting material is an oligomeric phenol. Like the polymeric phenols described above, oligomeric phenols used in the methods of the invention contain one or more crosslinked guaiacyl groups, and/or one or more crosslinked syringyl groups, and/or one or more crosslinked p-hydroxyphenyl groups. In general, oligomeric phenols will contain from about 2 to about 10 phenol subunits and will range in molecular weight ($M_w$) from about 200 g mol$^{-1}$ to 1,000 g mol$^{-1}$. One of skill in the art will appreciate that the average molecular weight of a particular oligomeric phenol starting material will depend on factors such as the source of the starting material and the method used for isolating the starting material from the source.

In some embodiments, the lignin-derived starting material is a monomeric phenol. Examples of monomeric phenols include, but are not limited to, examples of monomeric phenols include, but are not limited to, guaiacol, syringol, 4-ethylguaiacol (i.e., 4-ethyl-2-methoxyphenol), 4-vinylguaiacol (i.e., 2-methoxy-4-vinylphenol), eugenol (i.e., 4-allyl-2-methoxyphenol), 4-(1-propenyl)guaiacol (i.e., 2-methoxy-4-(prop-1-en-1-yl)phenol), vanillin (i.e., 4-hydroxy-3-methoxybenzaldehyde), allyl syringol (i.e., 4-allyl-2,6-dimethoxyphenol), and guaiacylacetone (i.e., 1-(4-hydroxy-3-methoxyphenyl)propan-2-one). As used herein, the term "guaiacol residue" refers to a monomeric guaiacyl radical which is not covalently bonded to other lignin-derived groups. As used herein, the term "syringol residue" refers to a monomeric syringyl radical which is not covalently bonded to other lignin-derived groups. As used herein, the term "hydroxyphenol residue" refers to a monomeric hydroxyphenyl radical which is not covalently bonded to other lignin-derived groups. A guaiacol residue, syringyl residue, or hydroxyphenyl residue can be bonded to compounds of the invention at a carbon atom or an oxygen atom of the residue.

A reaction mixture for forming a lignin-derived aminophenol can contain any suitable amount of the lignin-derived starting material. Typically, the amount of the lignin-derived starting material in the reaction mixture will range from about 1% (w/w) to about 90% (w/w), based on the total weight of the reaction mixture. The amount of the lignin-derived starting material can range, for example, from about 1% (w/w) to about 10% (w/w), or from about 10% (w/w) to about 20% (w/w), or from about 20% (w/w) to about 30% (w/w), or from about 30% (w/w) to about 40% (w/w), or from about 40% (w/w) to about 50% (w/w), or from about 50% (w/w) to about 60% (w/w), or from about 60% (w/w) to about 70% (w/w), or from about 70% (w/w) to about 80% (w/w), or from about 80% (w/w) to about 90% (w/w).

The amount of the lignin-derived starting material can range from about 1% (w/w) to about 70% (w/w), or from about 5% (w/w) to about 60% (w/w), or from about 10% (w/w) to about 50% (w/w). The amount of the lignin-derived starting material can range from about 1% (w/w) to about 25% (w/w), or from about 1% (w/w) to about 20% (w/w), or from about 1% (w/w) to about 15% (w/w). The amount of the lignin-derived starting material can range from about 2% (w/w) to about 8% (w/w), or from about (w/w) to about 7% (w/w), or from about 4% (w/w) to about 6% (w/w). The amount of the lignin-derived starting material can be about 1, 2, 3, 4, 5, 6, 7, 8, 9, 10, 11, 12, 13, 14, 15, 16, 17, 18, 19, or 20% (w/w), based on the total weight of the reaction mixture.

A number of carbonyl compounds can be used in the methods of the invention. Examples of suitable carbonyl compounds include, but are not limited to, formaldehyde (including paraformaldehyde), acetaldehyde, benzaldehyde, acetone, acetophenone, and the like. For example, the carbonyl compound can have the formula C(O)R$^a$R$^b$ wherein R$^a$ and R$^b$ are independently selected from hydrogen, C$_{1-12}$ alkyl, C$_{2-12}$ alkenyl, C$_{2-12}$ alkynyl, C$_{3-12}$ cycloalkyl, and C$_{6-14}$ aryl. In some embodiments, the carbonyl compound has the formula C(O)R$_2$, wherein R$^a$ and R$^b$ are independently selected from H and C$_{1-6}$ alkyl. Each of R$^a$ and R$^b$ can be, for example, H, methyl, ethyl, n-propyl, isopropyl, n-butyl, isobutyl, sec-butyl, tert-butyl, n-pentyl, branched pentyl, n-hexyl, or branched hexyl. In some embodiments, R$^a$ and R$^b$ are independently selected from H and methyl. In some embodiments, R$^a$ and R$^b$ are each H (i.e., the carbonyl compound is formaldehyde).

The reaction mixture can contain any suitable amount of the carbonyl compound. Typically, the amount of the carbonyl compound in the reaction mixture will range from about 1% (w/w) to about 90% (w/w), based on the total weight of the reaction mixture. The amount of the carbonyl compound can range, for example, from about 1% (w/w) to about 10% (w/w), or from about 10% (w/w) to about 20% (w/w), or from about 20% (w/w) to about 30% (w/w), or from about 30% (w/w) to about 40% (w/w), or from about 40% (w/w) to about 50% (w/w), or from about 50% (w/w) to about 60% (w/w), or from about 60% (w/w) to about 70% (w/w), or from about 70% (w/w) to about 80% (w/w), or from about 80% (w/w) to about 90% (w/w).

The amount of the carbonyl compound can range from about 1% (w/w) to about 70% (w/w), or from about 5% (w/w) to about 60% (w/w), or from about 10% (w/w) to about 50% (w/w). The amount of the carbonyl compound can range from about 1% (w/w) to about 25% (w/w), or from about 1% (w/w) to about 20% (w/w), or from about 1%

(w/w) to about 15% (w/w). The amount of the carbonyl compound can range from about 2% (w/w) to about 8% (w/w), or from about 3% (w/w) to about 7% (w/w), or from about 4% (w/w) to about 6% (w/w). The amount of the carbonyl compound can be about 1, 2, 3, 4, 5, 6, 7, 8, 9, 10, 11, 12, 13, 14, 15, 16, 17, 18, 19, or 20% (w/w), based on the total weight of the reaction mixture.

Any suitable amine can be used in the methods of the invention. In some embodiments, the amine is a secondary amine of the formula $NHR^cR^d$ wherein $R^c$ and $R^d$ are independently selected from $C_{1-12}$ alkyl, $C_{2-12}$ alkenyl, $C_{2-12}$ alkynyl, $C_{3-12}$ cycloalkyl, and $C_{6-14}$ aryl. In some such embodiments, $R^c$ and $R^d$ are each an independently selected $C_{1-12}$ alkyl, $R^c$ and $R^d$ can be, for example, methyl, ethyl, n-propyl, isopropyl, n-butyl, sec-butyl, isobutyl, tert-butyl, n-pentyl, branched pentyl, n-hexyl, branched hexyl, n-heptyl, branched heptyl, n-octyl, branched octyl, n-nonyl, branched nonyl, n-decyl, branched decyl, n-undecyl, branched undecyl, n-dodecyl, or branched dodecyl. Examples of amines for use in the methods of the invention include, but are not limited to, dimethylamine, diethylamine, diisopropylamine, and the like. In some embodiments, the amine is diethylamine.

Any suitable amount of the amine can be used in the methods of the invention. Typically, the amount of the amine in the reaction mixture will range from about 1% (w/w) to about 90% (w/w), based on the total weight of the reaction mixture. The amount of the amine can range, for example, from about 1% (w/w) to about 10% (w/w), or from about 10% (w/w) to about 20% (w/w), or from about 20% (w/w) to about 30% (w/w), or from about 30% (w/w) to about 40% (w/w), or from about 40% (w/w) to about 50% (w/w), or from about 50% (w/w) to about 60% (w/w), or from about 60% (w/w) to about 70% (w/w), from about 70% (w/w) to about 80% (w/w), or from about 80% (w/w) to about 90% (w/w).

The amount of the amine can range from about 1% (w/w) to about 70% (w/w), or from about 5% (w/w) to about 60% (w/w), or from about 10% (w/w) to about 50% (w/w). The amount of the amine can range from about 1% (w/w) to about 25% (w/w), or from about 1% (w/w) to about 20% (w/w), or from about 1% (w/w) to about 15% (w/w). The amount of the amine can range from about 2% (w/w) to about 8% (w/w), or from about 3% (w/w) to about 7% (w/w), or from about 4% (w/w) to about 6% (w/w). The amount of the amine can be about 1, 2, 3, 4, 5, 6, 7, 8, 9, 10, 11, 12, 14, 15, 16, 17, 18, 19, or 20% (w/w), based on the total weight of the reaction mixture.

In some embodiments, the lignin-based starting material, the carbonyl compound, and the amine are combined with a solvent in the reaction mixture. Examples of suitable solvents include, but are not limited to, water, dioxane, tetrahydrofuran, acetone, methanol, ethanol, butanol, ethylene glycol, and the like. In some embodiments, the solvent contains water. In some embodiments, the solvent contains water and at least one organic solvent selected from dioxane, tetrahydrofuran, acetone, methanol, ethanol, butanol, ethylene glycol. In some embodiments, the solvent consists of water. Typically, the pH of the reaction mixture containing the lignin-based starting material, the carbonyl compound, and the amine (in addition to a solvent, if present) will be alkaline, i.e., pH>7. As will be understood by those of skill in the art, the pH of the reaction mixture can be adjusted by the addition of one or more acids or bases. In some embodiments, the pH of the reaction mixture is adjusted to at least 8.0. In some embodiments, the pH of the reaction mixture is adjusted to at least 9.0. In some embodiments, the pH of the reaction mixture is adjusted to at least 10.0. In some embodiments, the pH of the reaction mixture is adjusted to at least 11.0.

The reaction mixture can be maintained at temperature suitable for forming the lignin-derived aminophenol. Typically, the reaction mixture will be maintained at a temperature ranging from about 25° C. to about 250° C. For example, the temperature can range from about 25° C. to about 50° C., or from about 50° C. to about 100° C., or from about 100° C. to about 150° C., or from about 150° C. to about 200° C., or from about 200° C. to about 250° C. The temperature can range from about 25° C. to about 100° C., or from about 30° C. to about 95° C., or from about 35° C. to about 90° C., or from about 40° C. to about 85° C., or from about 40° C. to about 80° C., or from about 35° C. to about 80° C., or from about 40° C. to about 75° C., or from about 45° C. to about 75° C., or from about 50° C. to about 70° C. The reaction mixture can be maintained at a temperature of about 25, 30, 35, 40, 45, 50, 55, 60, 65, 70, 75, 80, 85, 90, 95, or 100° C. Other temperatures may be used in the methods of the invention depending, in part, on factors such as the particular starting material, amine, and or carbonyl compound employed.

The mixture can be maintained under the reaction conditions for any length of time suitable for forming the lignin-derived aminophenol. Typically, the reaction mixture will be maintained for a period of time ranging from about 5 minutes to several hours, or longer. The period of time can range, for example, from about 15 minutes to about 30 minutes, or from about 30 minutes to about 45 minutes, or from about 45 minutes to about 60 minutes, or from about 60 minutes to about 75 minutes, or from about 75 minutes to about 90 minutes, or from about 90 minutes to about 105 minutes, or from about 105 minutes to about 120 minutes, or from about 120 minutes to about 135 minutes, or from about 135 minutes to about 150 minutes, or from about 150 minutes to about 165 minutes, or from about 165 minutes to about 180 minutes, or from about 180 minutes to about 195 minutes, or from about 195 minutes to about 210 minutes, or from about 210 minutes to about 225 minutes, or from about 225 minutes to about 240 minutes, or from about 240 minutes to about 255 minutes, or from about 255 minutes to about 270 minutes, or from about 270 minutes to about 285 minutes, or from about 285 minutes to about 300 minutes. The period of time can range from about 15 minutes to about 300 minutes, or from about 30 minutes to about 285 minutes, or from about 45 minutes to about 270 minutes, or from about 60 minutes to about 255 minutes, or from about 75 minutes to about 240 minutes, or from about 90 minutes to about 225 minutes, or from about 105 minutes to about 210 minutes, or from about 120 minutes to about 195 minutes, or from about 135 minutes to about 180 minutes, or from about 150 minutes to about 165 minutes.

The reaction mixture can be maintained under the reaction conditions for a period of time ranging from about 1 hours to about 2 hours, or from about 2 hours to about 4 hours, or from about 4 hours to about 6 hours, or from about 6 hours to about 8 hours, or from about 8 hours to about 10 hours, or from about 10 hours to about 12 hours, or from about 12 hours to about 16 hours, or from about 16 hours to about 20 hours, or from about 20 hours to about 24 hours, or from about 24 hours to about 28 hours, or from about 28 hours to about 32 hours, or from about 32 hours to about 36 hours, or from about 36 hours to about 40 hours, or from about 40 hours to about 44 hours, or from about 44 hours to about 48 hours. The period of time can range from about 1 hours to about 48 hours, or from about 2 hours to about 44 hours, or from about 4 hours to about 40 hours, or from about 6 hours to about 36 hours, or from about 8 hours to about 32 hours, or from about 10 hours to about 28 hours, or from about 12 hours to about 24 hours, or from about 16 hours to about 20 hours. The mixture can be maintained under the depolymerization conditions for about 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, or 52 hours.

The method of the invention further include converting the lignin-derived aminophenol to the lignin-derived ionic liquid. In some embodiments, the lignin-derived aminophenol in converted to the ionic liquid by contacting the lignin-derived aminophenol with an acid. The amino group of the lignin-derived aminophenol becomes protonated to form a cation, which pairs with the conjugate base of the acid (i.e., an anion), thereby forming the lignin-derived ionic liquid. In some such embodiments, the acid can be added directly to the reaction mixture following formation of the lignin-derived aminophenol. Alternatively, the lignin-derived aminophenol can be isolated from the reaction mixture prior to conversion to the ionic liquid. Any acid suitable for forming the lignin-derived ionic liquid can be used in the methods of the invention. Examples of suitable acids include, but are not limited to, mineral acids (e.g., hydrochloric acid, hydrobromic acid, phosphoric acid, and the like), carboxylic acids (e.g., acetic acid, propionic acid, glutamic acid, citric acid, maleic acid, and the like), and sulfonic acids (e.g., methanesulfonic acid, p-toluenesulfonic acid, and the like). In some embodiments, the acid is selected from hydrochloric acid, sulfuric acid, phosphoric acid, and combinations thereof. In some embodiments, the acid is hydrochloric acid. In some embodiments, the acid is sulfuric acid. In some embodiments, the acid is phosphoric acid.

Typically, an excess of acid will be added to the lignin-derived aminophenol in order to form the lignin-derived ionic liquid. In some embodiments, the lignin-derived aminophenol is combined with at least one molar equivalent of the acid. The lignin-derived aminophenol can be combined with at least 5, 10, 15, 20, 25, 50, 75, or 100 molar equivalents of the acid. Larger amounts of acid can also be employed, depending on factors including the structures of the particular aminophenol and the particular acid.

Other reactants can be used for converting the lignin-derived aminophenol to the lignin-derived ionic liquids. The lignin-derived aminophenol can be combined, for example, with borate salts, phosphate salts, phosphite salts, nitrate salts, sulfate salts, triflate salts, alkylated aluminates, halogenated aluminates, halogenated copperates, antimonates, galleates, substituted and unsubstituted carboxylate salts, substituted and unsubstituted carboranes, substituted and unsubstituted metalloboranes, poly-oxo metallates, and mixtures thereof.

Accordingly, lignin-derived ionic liquids prepared according to the methods of the invention may contain one more protonated aminophenol cations and one or more anions independently selected from the group consisting of $F^-$, $Cl^-$, $Br^-$, $HSO_4^-$, $BF_4^-$, $PF_6^-$, $NO_3^-$, $CF_3SO_3^-$, $CF_3COO^-$, $SbF_6^-$, $[CuCl_2]^-$, $AsF_6^-$, $SO_4^-$, $CF_3CH_2CH_2COO^-$, $(CF_3SO_2)_3C^-$, $CF_3(CF_2)_3SO_3^-$, $[CF_3SO_2]_2N^-$; $Al(R)_tX_{4-t}^-$ where R is $C_{1-12}$ alkyl and t is 0-4; $AlX_4^-$ where X is halogen; and $GaX_4^-$ where X is halogen. In some embodiments, the lignin-derived ionic liquid contains one or more protonated aminophenol cations and one or more anions independently selected from $Cl^-$ and $HSO_4^-$.

In a related aspect, the invention provides an ionic liquid containing at least one compound according to Formula I:

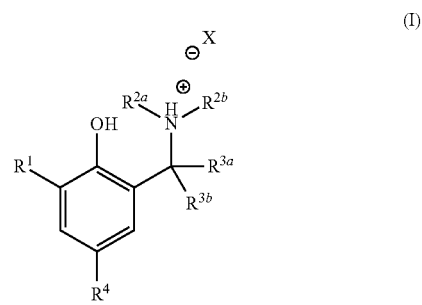

(I)

wherein:

$R^1$ is selected from the group consisting of $-OR^{1a}$ and hydrogen;

$R^{1a}$ is selected from the group consisting of $C_{1-6}$ alkyl and hydrogen;

$R^{2a}$ is selected from the group consisting of $C_{1-12}$ alkyl, $C_{2-12}$ alkenyl, $C_{2-12}$ alkynyl, $C_{3-12}$ cycloalkyl, and $C_{6-14}$ aryl;

$R^{2b}$ is selected from the group consisting of $C_{1-12}$ alkyl, $C_{2-12}$ alkenyl, $C_{2-12}$ alkynyl, $C_{3-12}$ cycloalkyl, $C_{6-14}$ aryl, and hydrogen;

$R^{3a}$ and $R^{3b}$ are independently selected from the group consisting of hydrogen, $C_{1-12}$ alkyl, $C_{2-12}$ alkenyl, $C_{2-12}$ alkynyl, $C_{3-12}$ cycloalkyl, and $C_{6-14}$ aryl;

$R^4$ is selected from the group consisting of a polymeric lignin residue, an oligomeric lignin residue, a guaiacol residue, a syringol residue, a hydroxyphenol residue, $C_{1-12}$ alkyl, $C_{1-12}$ alkoxy, $C_{2-12}$ alkenyl, $C_{2-12}$ alkynyl, and hydrogen; and X is an anion.

In some embodiments, $R^1$ is selected from the group consisting of $-OCH_3$ and hydrogen. In some embodiments, $R^{2a}$ and $R^{2b}$ are independently selected $C_{1-6}$ alkyl. In some embodiments, $R^{3a}$ and $R^{3b}$ are hydrogen. In some embodiments, $R^4$ is selected from the group consisting of an oligomeric lignin residue and a polymeric lignin residue. In some embodiments, $R^4$ is selected from the group consisting of a guaiacol residue, a syringol residue, and a hydroxyphenol residue. In some embodiments, X is selected from the group consisting of fluoride, chloride, bromide, a phosphate, a sulfate, a carboxylate, a fluorophosphate, and a fluoroborate. X is selected from the group consisting of chloride ($Cl^-$) and hydrogen sulfate ($HSO_4^-$).

One of skill in the art will appreciate that lignins and lignin-derived starting materials are complex mixtures of phenylpropane polymers and oligomers that vary in structure and molecular weight distribution. Accordingly, lignin-derived ionic liquids of the invention are often obtained as mixtures of compounds, e.g., mixtures of different compounds according to Formula I. For example, an ionic liquid of the invention can include 2, 3, 4, 5, 6, 7, 8, 9, 10, 20, 25, 30, 40, 50 or more different compounds according to Formula I (e.g., polymeric ionic liquids, oligomeric ionic liquids, monomeric ionic liquids, and combinations thereof).

III. EXAMPLES

Example 1

Synthesis of 2-(Dimethylaminomethyl)-6-methoxyphenol

In a 3 necked round bottom flask, paraformaldehyde (1.5 g, 0.05 mol) and diethylamine (3.7 g, 0.05 mol) were dissolved in 15 mL ethanol. The resulting solution was added dropwise to a solution of guaiacol (3.1 g, 0.025 mol) in ethanol (15 ml) at room temperature. After the addition was complete, the resulting reaction mixture was heated to 50° C. and stirred for 48 hrs. Then the reaction was cooled to room temperature and solvent was removed under reduced pressure. The crude product was acidified with 6M HCl and washed two times with ether and neutralized with $NaHCO_3$. The products were extracted with dichloromethane, dried over $MgSO_4$, and concentrated under vacuum.

Example 2

Synthesis of a Guaiacol-Based Ionic Liquid

To a stirred 2-(dimethylaminomethyl)-6-methoxyphenol (1.0 g, 5.0 mmol) in MeOH (25 mL) at 0° C. was slowly added $H_3PO_4$ (0.5 g, 5.0 mmol). The solution was allowed to stir, warming to room temperature for 3 h. Methanol was evaporated under vacuum and the ionic liquid was obtained as a light brown liquid (1.4 g, 93% yield).

Example 3

Synthesis of Lignin-Based Polymeric Ionic Liquid

In a 100 mL 3 necked round bottom flask, 2.0 g of lignin, 3.0 g of diethylamine, and 50 mL of distilled water were added. The pH of the mixture was adjusted to 11 and stirred for 30 min. To the reaction mixture, 2.0 g of 37% formaldehyde solution was added stepwise at room temperature. After the addition of formaldehyde, the reaction mixture was heated to 60° C. for 6 h. Then the reaction mixture was cooled to room temperature and the pH of the mixture was adjusted to 2-3 with 10 vol % HCl (or $H_2SO_4$) and stirred for additional 30 mins. After that, the solution was added to about 100 mL of isopropyl alcohol, the precipitate was recovered by vacuum filtration and washed with isopropyl alcohol, and then dried in a vacuum at 50° C. for 48 hrs to generate the lignin-based polymeric ionic liquid.

Although the foregoing has been described in some detail by way of illustration and example for purposes of clarity and understanding, one of skill in the art will appreciate that certain changes and modifications can be practiced within the scope of the appended claims. In addition, each reference provided herein is incorporated by reference in its entirety to the same extent as if each reference was individually incorporated by reference.

What is claimed is:

1. An ionic liquid comprising at least one compound according to Formula I:

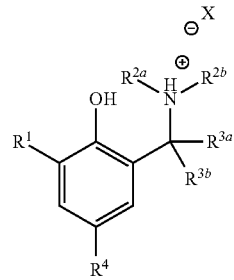

(I)

wherein:
$R^{2a}$ is selected from the group consisting of $C_{1-12}$ alkyl, $C_{2-12}$ alkenyl, $C_{2-12}$ alkynyl, $C_{3-12}$ cycloalkyl, and $C_{6-14}$ aryl;
$R^{2b}$ is selected from the group consisting of $C_{1-12}$ alkyl, $C_{2-12}$ alkenyl, $C_{2-12}$ alkynyl, $C_{3-12}$ cycloalkyl, $C_{6-14}$ aryl, and hydrogen;
$R^{3a}$ and $R^{3b}$ are independently selected from the group consisting of hydrogen, $C_{1-12}$ alkyl, $C_{2-12}$ alkenyl, $C_{2-12}$ alkynyl, $C_{3-12}$ cycloalkyl, and $C_{6-14}$ aryl;
$R^4$ is a polymeric lignin residue; and
X is an anion.

2. The ionic liquid of claim 1, wherein $R^{2a}$ and $R^{2b}$ are independently selected $C_{1-6}$ alkyl.

3. The ionic liquid of claim 1, wherein $R^{3a}$ and $R^{3b}$ are hydrogen.

4. The ionic liquid of claim 1, wherein X is selected from the group consisting of fluoride, chloride, bromide, a phosphate, a sulfate, a carboxylate, a fluorophosphate, and a fluoroborate.

5. The ionic liquid of claim 1, comprising two or more different compounds according to Formula I.

6. A method for preparing a lignin-derived ionic liquid according to Formula I,

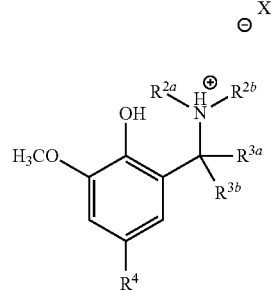

(I)

the method comprising:
forming a reaction mixture comprising a lignin-derive d starting material, a carbonyl compound, and an amine;
maintaining the reaction mixture under conditions sufficient to form a lignin-derived aminophenol; and
converting the lignin-derived aminophenol to the lignin-derived ionic liquid; wherein:
$R^{2a}$ is selected from the group consisting of $C_{1-12}$ alkyl, $C_{2-12}$ alkenyl, $C_{2-12}$ alkynyl, $C_{3-12}$ cycloalkyl, and $C_{6-14}$ aryl;

$R^{2b}$ is selected from the group consisting of $C_{1-12}$ alkyl, $C_{2-12}$ alkenyl, $C_{2-12}$ alkynyl, $C_{3-12}$ cycloalkyl, $C_{6-14}$ aryl, and hydrogen;

$R^{3a}$ and $R^{3b}$ are independently selected from the group consisting of hydrogen, $C_{1-12}$ alkyl, $C_{2-12}$ alkenyl, $C_{2-12}$ alkynyl, $C_{3-12}$ cycloalkyl, and $C_{6-14}$ aryl;

$R^4$ is a polymeric lignin residue; and

X is an anion.

7. The method of claim 6, wherein the carbonyl compound is selected from the group consisting of a ketone and an aldehyde.

8. The method of claim 6, wherein the amine is a primary amine or a secondary amine.

9. The method of claim 6, wherein the reaction mixture further comprises a solvent.

10. The method of claim 9, wherein the solvent is water.

11. The method of claim 6, wherein the reaction mixture consists of the lignin-derived starting material, the carbonyl compound, and the amine.

12. The method of claim 6, wherein the reaction mixture is maintained at a temperature ranging from about 25° C. to about 250° C. for a period of time ranging from about 5 minutes to about 24 hours.

13. The method of claim 6, wherein converting the lignin-derived aminophenol to the ionic liquid comprises contacting the lignin-derived aminophenol with an acid.

14. The method of claim 13, wherein the acid is hydrochloric acid, sulfuric acid, or a combination thereof.

15. The method of claim 6, further comprising isolating at least a portion of the ionic liquid.

* * * * *